United States Patent
Schreier et al.

(10) Patent No.: US 10,342,922 B2
(45) Date of Patent: Jul. 9, 2019

(54) DEVICE AND METHOD FOR PRODUCING, DOSING AND PACKAGING MEDICAMENTS

(71) Applicant: AIT AUSTRIAN INSTITUTE OF TECHNOLOGY GMBH, Vienna (AT)

(72) Inventors: Guenter Schreier, Graz (AT); Robert Modre-Osprian, Ligist (AT)

(73) Assignee: AIT Austrian Institute of Technology GmbH, Vienna (AT)

( * ) Notice: Subject to any disclaimer, the term of this patent is extended or adjusted under 35 U.S.C. 154(b) by 815 days.

(21) Appl. No.: 14/443,141

(22) PCT Filed: Nov. 12, 2013

(86) PCT No.: PCT/AT2013/050217
§ 371 (c)(1),
(2) Date: May 15, 2015

(87) PCT Pub. No.: WO2014/075119
PCT Pub. Date: May 22, 2014

(65) Prior Publication Data
US 2015/0258276 A1    Sep. 17, 2015

(30) Foreign Application Priority Data

Nov. 15, 2012 (AT) ............... A 50516/2012

(51) Int. Cl.
| | | |
|---|---|---|
| A61M 5/172 | (2006.01) |
| A61J 1/03 | (2006.01) |
| A61J 3/00 | (2006.01) |
| A61B 5/0205 | (2006.01) |
| A61B 5/021 | (2006.01) |
| A61B 5/0452 | (2006.01) |
| A61B 5/11 | (2006.01) |
| A61B 5/145 | (2006.01) |
| A61B 5/16 | (2006.01) |
| A61B 5/00 | (2006.01) |
| A61F 7/00 | (2006.01) |
| A61N 5/06 | (2006.01) |
| A61N 5/10 | (2006.01) |
| B65B 3/00 | (2006.01) |
| B65B 7/16 | (2006.01) |
| B65D 75/36 | (2006.01) |

(52) U.S. Cl.
CPC ........... *A61M 5/1723* (2013.01); *A61B 5/021* (2013.01); *A61B 5/0205* (2013.01); *A61B 5/0452* (2013.01); *A61B 5/1118* (2013.01); *A61B 5/145* (2013.01); *A61B 5/165* (2013.01); *A61B 5/4824* (2013.01); *A61F 7/00* (2013.01); *A61J 1/035* (2013.01); *A61J 3/00* (2013.01); *A61J 3/005* (2013.01); *A61N 5/06* (2013.01); *A61N 5/10* (2013.01); *B65B 3/003* (2013.01); *B65B 7/16* (2013.01); *B65D 75/367* (2013.01); *A61J 2200/30* (2013.01); *A61J 2205/60* (2013.01); *A61M 2230/005* (2013.01); *A61M 2230/06* (2013.01); *A61M 2230/30* (2013.01); *A61M 2230/63* (2013.01)

(58) Field of Classification Search
CPC .................................... A61M 5/1723
USPC .......................................... 702/19
See application file for complete search history.

(56) References Cited

U.S. PATENT DOCUMENTS

| 2008/0135446 A1 | 6/2008 | Pohl |
| 2008/0197042 A1 | 8/2008 | Ullrich |

FOREIGN PATENT DOCUMENTS

| WO | 2006007867 A1 | 1/2006 |
| WO | 2007070902 A1 | 6/2007 |
| WO | 2009000425 A2 | 12/2008 |
| WO | 2009018922 A1 | 2/2009 |
| WO | 2013110107 A1 | 8/2013 |

*Primary Examiner* — Jerry Lin
(74) *Attorney, Agent, or Firm* — Laurence A. Greenberg; Werner H. Stemer; Ralph E. Locher (57) ABSTRACT

A method produces a number of medicaments with a predetermined active substance and for simultaneously making an active substance value indicating the active substance quantity contained in the medicament available. A standard value is determined for the active substance quantity of the medicaments and a maximum deviation from the standard value is predefined. An active substance value is selected within an interval $cN+/-\Delta c$ or predefined and an active substance quantity is used as a reference for the preparation of the respective medicament which quantity matches the active substance value. The active substance value established is associated with the medicament and is held available together with the medicament once the medicament is prepared.

11 Claims, 3 Drawing Sheets

DEVICE AND METHOD FOR PRODUCING, DOSING AND PACKAGING MEDICAMENTS

BACKGROUND OF THE INVENTION

Field of the Invention

The invention relates to a method for producing medicaments according to the preamble of the main method patent claim. Furthermore, the invention relates to a combination with a medicament blister and storage according to the preamble of the main medicament patent claim. Finally, the invention relates to a device for producing medicaments according to the preamble of the main device patent claim. The invention also relates to a device for carrying out a therapy according to the preamble of the main therapy device patent claim.

BRIEF SUMMARY OF THE INVENTION

The invention as well as individual methods, combinations and devices according to the present invention are used in the field of analysis of the effectiveness as well as in the field of compliance- and adherence-measurements of medicaments or treatments.

The starting point of the invention is a method for determining the sensitivity of a therapeutic measured variable of a person to change of a therapeutic control variable during the therapy. The treatment intensity corresponds—in analogy to control engineering—to the respective control variable, the physiological value to be set, for example, the blood pressure value, corresponds to the measured variable to be controlled.

In medical therapeutics, it is common, to have an influence on different physiological measured variables of patients with the aid of therapeutic control variables. For example, patients are prescribed medications in a certain doses—this is the control variable with which the blood pressure is influenced—this is the measured variable. The degree of influence of the measured variable can be measured continuously or selectively, invasively or non-invasively with the aid of suitable methods, for example, the systolic and diastolic blood pressure by means of an electronic blood pressure monitor.

Assuming that all other influencing factors remain constant, it can be assumed, that the relationship between control variable and measured variable m can be represented as a "control variable-measured variable curve." In the pharmaceutical field this relationship is called the dose-response curve. Generalizing, the term treatment intensity also stands for all therapeutic control variables, which are used in this connection.

Figure 1:
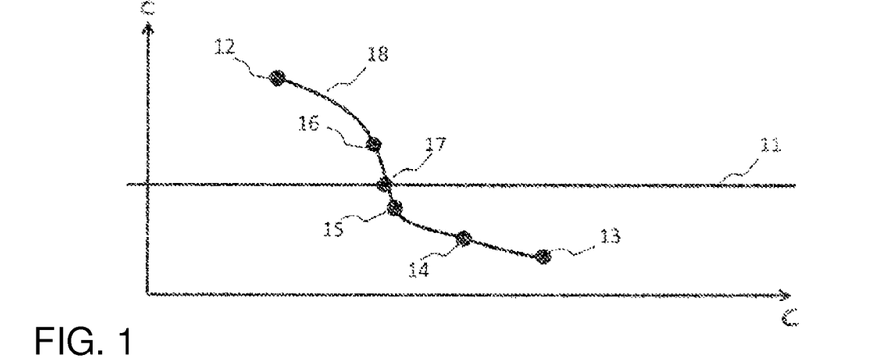
FIG. 1 is a graph showing a therapeutic control variable curve determined by a first method.
Figure 2:
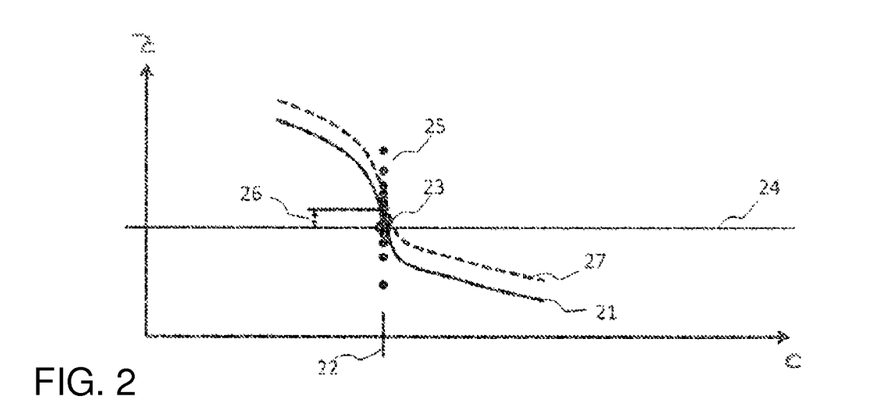
FIG. 2 is a graph showing a therapeutic control variable curve determined by a second method.

The prior art is elucidated in detail by means of two common methods. FIG. 1 shows a therapeutic control variable-measured variable curve determined based on a first method. FIG. 2 shows a therapeutic control variable-measured variable curve determined based on a second method.

In FIG. 1 it is shown, for example, how a control variable-measured variable curve can be determined in the course of a treatment. If, for example, a patient is adjusted to a new antihypertensive medication or medicament, a specific target-value of the measured variable z, in the present case a specific blood pressure value, should be achieved. For this purpose, the doctor selects an initial dose of the medication as therapeutic control variable c and measures, if necessary time-delayed after the in-take phase, the blood pressure resulting therefrom as physiological measured variable z. The first point of the control variable-measured variable curve 12 can be derived from this. Depending on the initial value of the measured variable z, the treatment intensity or the control variable c is then adjusted and the measured variable z is measured again. This process is repeated and measured variables z: 14, 15, 16 are determined for additional control variables, until that value of the control variable was found, which leads to the desired value of the measured variable. Thus, the dose c of the medication is therefore found, in which the desired blood pressure z is attained for the respective patient. This desired value is also called working point 17 in an analogy to control engineering. By connecting the points, the respective coordinate values of which correspond to control variable c or measured variable z, a graph is obtained, as depicted in FIG. 1, the control variable-measured variable curve 18.

In the course of this adjustment process, individual points of the control variable-measured variable curve are therefore determined. The measured variables z at different control variables are compared with each other and also the sensitivity of the measured variable z to changes in the control variable can be considered. The sensitivity of the measured variable z to changes in the control variable c corresponds to the slope of the control variable-measured variable curve 18. Each value of the control variable c is set thereby once and by increasing or decreasing the control variable c, with each measurement a new measuring point is found on the control variable-measured variable curve 18.

In a scenario in the insulin treatment of diabetics an individual control variable-measured variable curve is determined during the adjustment process. During the therapy, at predetermined times, the patient measures his blood sugar level as measured variable z and subsequently injects that amount c of insulin, which is necessary according to the relationship between control variable and measured variable z obtained from personal experience and medical knowledge, in order to attain the desired value of the measured variable. With each intake of medication and associated blood sugar measurement, thus also even during the ongoing therapy, a point in the control variable-measured variable curve is determined—the curve can thus constantly be adjusted to possible changes.

However, such an approach can lead to dangerous effects precisely when measuring the sensitivity of a person with respect to changes in the dosage of insulin, since already slight under- and overdoses can cause severe complications.

It is therefore customary, as depicted in FIG. 2, no longer to change a medication after the initial setting and to refrain from possible dangers to the patient. As soon as the adequate value of the control variable 22 as well as the associated initial control variable-measured variable curve 21 was found, the medication of the patient is no longer changed for perhaps a long time and the value of the control variable is maintained.

If the control variable-measured variable curve were temporally invariant and not influenced by other factors, due to the constant control variable 22 at each individual measurement of the measured variable z, one and the same, desired value 24 would be measured and all control variable-measured variable pairs would be located at the working point 23. However, for several reasons the measured variable z also varies at a constant control variable: in general, disturbance values also influence the measured variable z, for example, time of day, diet, external factors, physical activity, etc. In addition, the measurement is often affected by measurement inaccuracies. As a result, values of the measured variable z deviating from the desired value of the measured variable are therefore measured at the working point at different times and a "one-dimensional point cloud" 25 arises, which has points each with the identical control variable.

Assuming that the control variable-measured variable curve does not change with time, and that disturbance values and measurement errors are distributed stochastically, the average measured variable of the measured variable z will continue to be the desired value of the measured variable z. However, if the control variable-measured variable curve changes with time—for example, because the body of the patient is accustomed to an administered medication and the effectiveness of the medication diminishes with time—the average value of the measured variable z, which is measured, consequently shifts from the working point.

If it is found, that, for example, due to this habituation effect the medication of the patient changes and thus the working point must be shifted, as a rule no information is available on this, as to how the control variable-measured variable curve has changed in the meantime.

In general, no definite statement can be made concerning the changed curve and on how much a slight change in the control variable-measured variable curve—from the working point—could have an impact on the measured variable z, i.e. what slope the control variable-measured variable curve has at the working point.

The problem addressed by the invention is to provide suitable medicaments or devices, with which a measurement of the individual dose-response curve of a patient is made possible, wherein the dose-response curve can be determined continually at a working point, without disturbing the actual treatment and endangering the patients.

The invention solves this problem with a method mentioned at the outset with the characterizing features of the main method patent claim. Furthermore, the invention solves the problem with a combination mentioned at the outset of a medicament blister and storage with the characterizing features of the main medicament patent claim. Further, the invention solves this problem with a device for producing medicaments of the type mentioned at the outset with the characterizing features of the main device patent claim. Finally, the invention solves this problem with a device for producing medicaments of the type mentioned at the outset with the characterizing features of the main therapy device patent claim.

According to the present invention, with a method is provided for producing a number of medicaments with a predetermined active substance as well as for simultaneously making available an active substance value indicating the respective active substance quantity contained in the medicament, that a standard value to be determined for the active substance quantity of the medicaments and a maximum deviation from this standard value are predefined, wherein an active substance value is selected or predefined within an interval $c_N+/-\Delta c$ and an active substance quantity is used as a reference for the preparation of the respective medicament, which quantity matches the active substance value, and that active substance value established is associated with the medicament and is kept available together with the medicament once the medicament is prepared.

With a medicament or medication obtained according to the present invention the respective dose-response curve can be determined. After the administration of the thus-created medications determined physiological measured variables can be put in relation to the active substance values created with the method according to the present invention, whereby a control variable-measured variable curve, particularly a dose-response curve can easily be determined, without changing the basic adjustment of the dosage or the working point of the dosage.

Advantageously, it can be provided to achieve significant dose-response curves on the basis of the medicament created, that the active substance values of the individual medicaments are predefined as, in particular following a predetermined distribution, in particular uniformly distributed or discretely distributed, random values within a predefined interval $c_N+/-\Delta c$.

For the precise determination of the slope of the control variable-measured variable curve at the working point it can be provided, that the maximum deviation from the standard value is greater than 5%, in particular, greater than 10% of the standard value.

An especially accurate dosage and handling can be achieved with a medicament available in liquid form. In this connection it is provided that—that an active substance fluid containing the active substance, in particular a solution, emulsion or suspension, as well as a number of excipients, in particular powder tablets, are made available, that a predefined quantity of the active substance fluid is dripped onto the excipient and is received by the excipient substance of the excipient, wherein during the fall of the respective droplet in the direction of the excipient the volume of the respective droplet is determined, and that for the respective medicament the respective size of the droplet is assigned as an active substance value to the medicament created and the medicament is kept available together with the active substance value associated to it.

In order to make possible a personalization of the medicament to be dispensed or dispensed and a direct statement about the patient, it can be provided, that the medicaments created are assigned to a patient, preferably dispensed to the patient, and the respective active substance value together with the respective dispensing time are stored in a documentation storage assigned to the respective patient.

In this connection it is also advantageous, that medicaments can be immediately produced and dispensed to a patient.

In order to make possible the production of the medicaments and a subsequent packaging of the medicament in medicament blisters, it can be provided that—that the medicament created after its production is inserted into a predetermined pocket of a medicament blister, in particular of a medicament blister, that the active substance value associated with the medicament as well as a key characterizing the predetermined respective pocket of the medicament blister are jointly transmitted to a storage located preferably on a controller located on the medicament blister, and that a key characterizing the respective pocket as well as the respective active substance quantity of the medicament located in the respective pocket, are kept available for retrieval, in particular by the controller.

It can be provided for monitoring the intake, that the pockets of the medicament blister containing the medicaments are closed after insertion of the medicament, and before taking the medicament the respective pocket is opened by the patient, that the opening of the respective pocket is detected by the controller located on the medicament blister, that the respective active substance value of the medicament located in the pocket last opened is kept available separately and/or additionally, in particular by the controller, and that, if necessary, the respective active substance value together with the respective dispensing time is stored in a documentation storage of the documentation server assigned to the respective patent.

Alternatively, in order to make possible the production of the medicament and a subsequent packaging of the medicament in medicament blisters, it can also be provided,—that the medicament created is inserted into a predetermined pocket of the medicament blister, which has a controller, on which a predetermined identification $(m_1, \ldots, m_n)$ characterizing the medicament blister is stored, that the active substance quantity $(c_1, \ldots, c_n)$ associated with the medicament, the identification $(m_1, \ldots, m_n)$ associated with the respective medicament blister, as well as a key $(k_1, \ldots, k_n)$ characterizing the predetermined respective pocket of the medicament blister are transmitted jointly to a server, and that the respective active substance value $(c_1, \ldots, c_n)$ of the medicament located in the respective pocket during transmission of the identification $(m_1, \ldots, m_n)$ characterizing the medicament blister as well as of the key $(k_1, \ldots, k_n)$ characterizing the respective pocket are kept available for retrieval by the server. In this case, it can be provided for monitoring the intake, that—that the pockets of the medicament blister containing the medicament are closed after the insertion of the medicament, and the respective pocket is opened by the patient before taking the medicament, that the respective opened pocket is detected by the controller located on the medicament blister, that the respective key $(k_1, \ldots, k_n)$ of the last opened pocket jointly with the identification (m) of the respective medicament blister is transmitted to the server and the server determines and keeps available the active substance quantity $(c_1, \ldots, c_n)$ stored on it and associated with the key as well as the identification (m), and that, if necessary, the respective active substance value is transmitted to a control variable storage unit, wherein the respective active substance value together with the respective dispensing time are stored in a storage of the control variable storage unit assigned to the respective patient.

Furthermore, the invention relates to a combination comprising at least one medicament blister comprising a number of medicaments, in particular, tablets or capsules, which are arranged in pockets formed in the medicament blister, and in particular containing exclusively the respective medicament, wherein the individual medicaments in each case have a different active substance quantity $(c_1, \ldots, c_n)$. This combination comprises a storage, which in each case for each of the pockets of the medicament blister has in each case a storage space, in which an active substance value $(c_1, \ldots, c_n)$ is stored, which corresponds to the active substance quantity of the medicament located in the respective pocket, wherein the storage keeps available upon request during the transmission of an identification $(m_1, \ldots, m_n)$ clearly characterizing the pocket the respective active substance value (c) associated with the medicament in the respective pocket. Such a combination of a medicament blister and its storage can be used advantageously for the determination of dose-response curves. In particular, the respective medication dose as an active substance value is available for each medication taken or to be taken. In order to measure the connection between dosage and effect of the medicament, the respective medicament can be administered to the patient and subsequently the effects can be determined and quantified, for example, by measurement of the blood pressure in the case of an antihypertensive medication. Since the medication dose is available for the respective medication in an easily retrievable manner via the storage, the dose-response curve can be rapidly created and kept available for new therapeutic recommendations.

In order to detect which of several medicaments was removed from a container and in order to obtain the active substance value to be used for the dose-response curve, it can be provided that a controller is provided on the medicament blister, a) wherein on the controller an identification $(m_1, \ldots, m_n)$ clearly characterizing the medicament blister is stored and/or b) wherein the controller monitors the opening of pockets formed on the medicament blister and keeps available the identification $(m_1, \ldots, m_n)$ clearly characterizing the in each case last opened pocket.

An easy option of access to the individual active substance values provides, that the storage is integrated into the controller arranged on the medicament blister, wherein in each case a storage area is provided in the storage for each medicament located in the individual pockets, in which the respective active substance quantity $(c_1, \ldots, c_n)$ of the medicament is stored, and that upon request the controller indicates the respective active substance quantity $(c_1, \ldots, c_n)$ of the medicament located in the respective pocket by specifying a key $(k_1, \ldots, k_n)$ characterizing the respective pocket.

Alternatively, it can be provided for the same purpose, that the controller formed on the medicament blister has an identification storage, on which an identification $(m_1, \ldots, m_n)$ clearly characterizing the medicament blister is provided, that the storage is formed on a server, wherein the server, if necessary, has a number of storages, wherein each storage is assigned in each case to a medicament blister, wherein in each case a storage area is provided in the respective storage provided for the medicament blister for each medicament located in the individual pockets of the medicament blister, in which the respective active substance value $(c_1, \ldots, c_n)$ of the medicament located in the pocket of the medicament blister is stored, and that the server upon request transmits the respective active substance quantity $(c_1, \ldots, c_n)$ of the medicament located in the respective pocket by specifying the identification $(m_1, \ldots, m_n)$ characterizing the medicament blister as well as a key $(k_1, \ldots, k_n)$ characterizing the respective pocket of the medicament blister.

Furthermore, this also makes it possible, that the opening of the individual medicament blister can be monitored centrally, as well as makes possible simple central data storage as well as a concomitant increased protection against falsification.

Advantageously, it can be provided to achieve significant dose-response curves on the basis of the medicament created, that the active substance values (c) of the individual medicaments follow a predetermined distribution within the interval $c_N +/- \Delta c$, for example, are uniformly distributed or discretely distributed.

For the precise determination of the slope of the control variable-measured variable curve at the working point it can be provided that the maximum deviation $\Delta c$ from the standard value $c_N$ is greater than 5%, in particular, greater than 10% of the standard value.

Finally, the invention also relates to a device for producing medicaments. According to the present invention, a device is provided for producing medicaments comprising a) a supply unit for the provision of excipients, in particular powder tablets, b) a portioning unit for portioning the active substance, in particular an active substance fluid, as well as for applying the active substance, in particular for dripping the active substance fluid the excipient provided by the supply unit: c) a control unit for controlling the size of the quantity of the active substance supplied by the portioning unit, in particular droplets, wherein the control unit sets a standard value ($c_N$) for the active substance quantity of the medicament to be set in each case, and the control unit of the portioning unit in each case provides an active substance quantity to be applied within an interval around the standard value ($c_N$), wherein the control unit keeps available the predetermined active substance quantity or the active substance quantity contained in the medicament as active substance value (c) of the medicament created after its creation and stores it permanently in a storage provided therefor.

With such a device medicaments can be produced easily and rapidly, the respective active substance value of which is known and can be used for the creation of a dose-response curve.

In order to obtain medications with a predetermined and in particular adjustable deviation of the dose as well as of the active substance value, it can be provided, that the control unit is designed for controlling the size of the quantity of the active substance supplied by the portioning unit, that the control unit for the active substance quantity of the medicament to be set in each case sets a standard value ($c_N$) and a maximum deviation $\Delta c$ from this standard value, that the control unit of the portioning unit provides in each case an active substance quantity to be applied, in particular a random value ($c_R$) within the interval $c_N +/- \Delta c$ as active substance value (c), wherein the control unit keeps available the predetermined active substance value (c) after the creation of the medicament.

In order to use the natural production tolerance of an existing portioning unit, it can be provided that the portioning unit is designed for portioning of active substance fluid as well as for dripping of active substance fluid on the excipients already made available by the supply unit, and the portioning unit dispenses the droplets of the active substance fluid with a predetermined average droplet size ($C_N$) and a known maximum deviation $\Delta c$ from the predetermined average droplet size ($C_N$), and that the control unit is provided a unit for determining the droplet size of droplets applied by the portioning unit on the excipients, which keeps available the size of the respective droplets applied to the excipients as active substance value (c).

To record a dose-response curve, the invention provides a further method for determining the sensitivity of a patient to a therapy. In this connection, it is provided that the respective medicament is administered to the patient, wherein after taking the medicament in each case a physiological measured variable (z) of the patient is determined and assigned to the active substance value (c), and wherein for all physiological measured variables (z) and active substance values (c) assigned to each other a sensitivity (F) is determined in each case, which corresponds in the range of the standard value ($C_N$) to the relative increase (dz/dc) of the physiological measured variables (z) in the case of an increase of the respective active substance value (c).

With this method, not only a generally advantageous treatment can be carried out, it is also still possible, in the case of a setting of the treatment intensity made once, to make the statement, how sensitively the therapeutic measured variable will respond to slight changes in the treatment intensity in the range of a given treatment intensity.

In order to be able to record the respective effect, it can be provided, that the blood pressure, body weight, ECG parameters, blood values, stress parameters, pain parameters, depression level, flexibility of specific joints as well as the mobility of the patient, measurements for the wellbeing of the patient or combinations thereof are consulted as physiological parameters.

In order to be able to better record the temporal delay of the effect of a medicament, it can be provided, that the respective parameter is determined a specific time period after dispensing the respective medicament in the body.

To record a dose-response curve the invention also provides a device for determining the sensitivity of a patient to a therapy. In this connection, it is provided, that a) a therapy administration unit comprising a therapy administration control sets a treatment intensity and, if necessary, a variation of the treatment intensity, wherein the treatment unit performs a treatment on a patient with the predetermined treatment intensity with a variation of the treatment intensity due to its design or predetermined by the therapy administration unit, b) a control variable storage unit downstream of the therapy administration unit and/or its treatment unit for storage of the respective treatment intensity subject to a variation, c) a measured variable measuring unit for determining a physiological measured variable by measuring the patient treated, d) a measured variable storage unit downstream of the measured variable measuring unit for storage of the respective determined physiological measured variable, as well as e) an evaluation unit downstream of the control variable storage unit and the measured variable storage unit for determining the relationship between the stored treatment intensities and the physiological measured variables, in particular, for determining the effects of changes of the treatment intensity on the physiological measured variables. With this method, not only a generally advantageous treatment can be carried out, it is also still possible, in the case of a setting of the treatment intensity made once, to make the statement, how sensitively the therapeutic measured variable will respond to slight changes in the treatment intensity in the range of a given treatment intensity.

An advantageous aspect of the invention provides that a control variable measuring unit determines the control variable emitted by the therapy administration control or the treatment unit and keeps it available for storage by the control variable storage unit. Such a device can be easily created and be used for diverse treatments.

In order to obtain a personal dose-response curve, it can be provided, that the control variable storage unit and the measured variable storage unit keep available for each patient a separate storage area and the downstream evaluation unit in determining the relationship between the stored treatment intensities and the physiological measured variables has access to stored treatment intensities and physiological measured variables of the same person exclusively, which in each case are stored in storage areas which are separate and assigned to this person.

Some embodiments of the invention are described in more detail by means of the following drawings.

Figure 3:
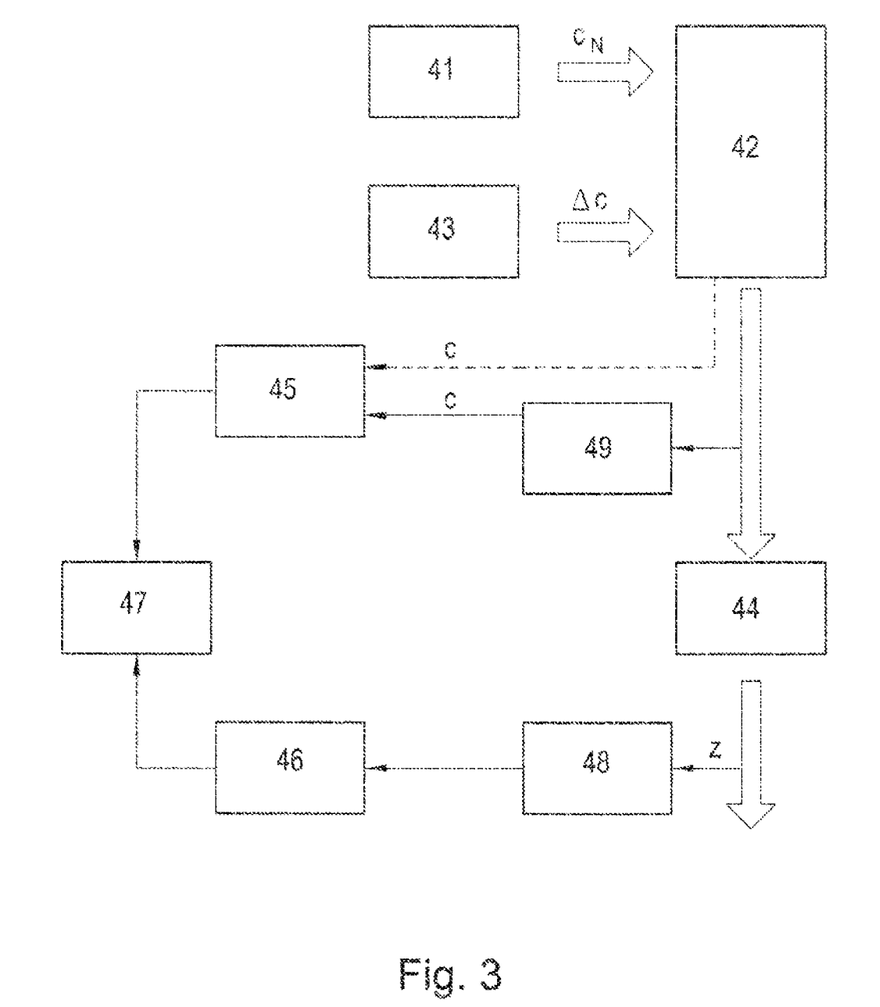
FIG. 3 is a flow chart showing a process treatment according to the invention.
Figure 4:
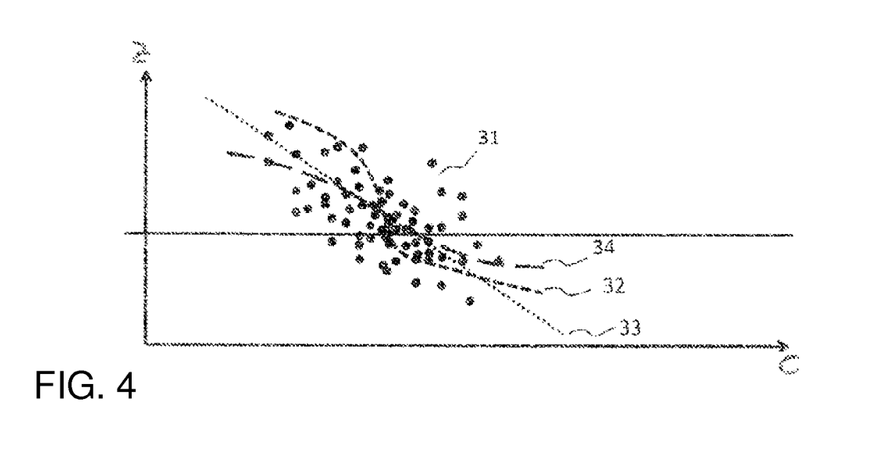
FIG. 4 is a graph showing a dose-response curve determined according to the invention.
Figures 5, 6, 7, 8:
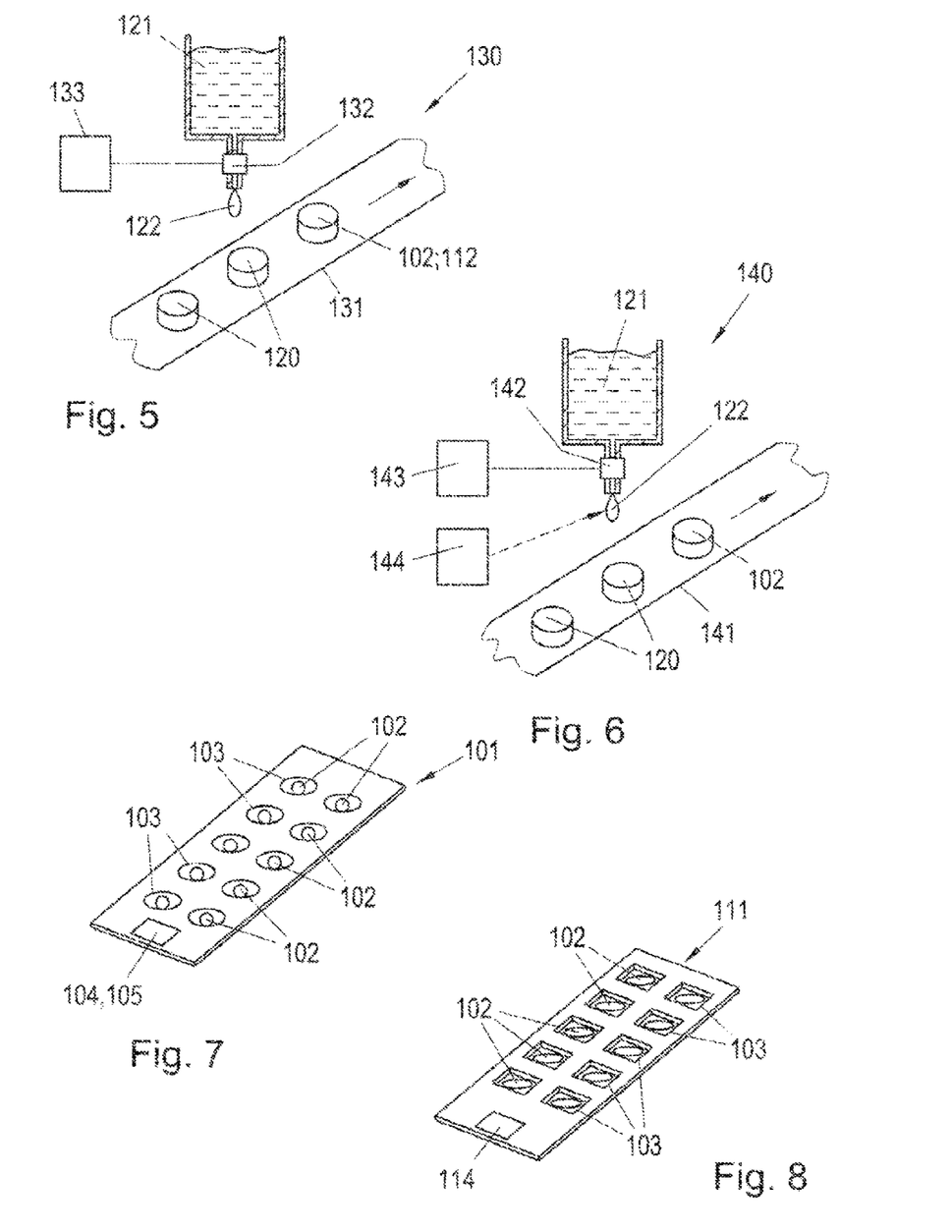
FIG. 5 is a perspective view of a process for producing medicaments.
FIG. 6 is a perspective view of a process for producing medicaments.
FIG. 7 is a perspective view of a first embodiment of a medicament blister.
FIG. 8 is a perspective view of a second embodiment of the medicament blister.

In FIG. 3 the process of a treatment is depicted schematically. FIG. 4 shows the dose-response curve determined in the method depicted in FIG. 3. FIGS. 5 and 6 show different embodiments for producing medicaments. FIGS. 7 and 8 show two different medicament blisters produced with a method according to the present invention.

DESCRIPTION OF THE INVENTION

In FIG. 3 the process of a treatment as well as the evaluation of the individual measured variables are depicted schematically, which forms the starting point of the invention. A doctor 41 determines a treatment intensity, for example, a medicament dose, a radiation dose, training duration for exercises, etc. Through this treatment intensity an initial control point is preset, with which a specific physiological target value shall be achieved. Then the doctor 41 can, for example, with the setting of a dosage of a medication, wish to achieve a reduction of the systolic blood pressure value to a specific standard value. Since, however, different patients 44 respond differently to the respective medication administered, the effect of the medication can be stronger or weaker than expected by doctor 41, so that after a specific time a correction of the treatment intensity is required. Thus, doctor 41 can, for instance, reduce the daily dosage, in order to prevent a too-low setting of the blood pressure in the case of a too strong response of the patient 44 to the medicament.

As already mentioned, the doctor 41 at an initial point in time sets both the control variable or the treatment intensity as well as the desired measured variable z. In addition to the control variable $c_N$ and the measured variable z, the doctor also sets a variation $\Delta c$ of the control variable c. Both the control variable $c_N$ preset by the doctor as a working point setting as well as the variation setting $\Delta c$, which is transmitted by a variation unit 43, are fed to the therapy administration unit 42. From these values $c_N$, $\Delta c$ the therapy administration unit 42 determines a control variable c or treatment intensity c within the interval $c_N +/- \Delta c$. A therapy with this treatment intensity is administered to the patient 44 in the context of the respective therapy administration unit 42.

The actual value of the control variable c, that is, including the in each case impressed variation, as well as the time of the administration is stored in a control variable storage unit 45. The information can either be determined indirectly from the setting of the therapy administration unit 42 influenced by the variation unit 43 or directly by measurement of the actual value of the control variable by means of the control variable measuring unit 49.

Subsequently, the measured variable z, for example, the blood pressure is measured via a measured variable measuring unit 48 and the value and the measuring time is stored in a measured variable storage unit 46. From the values for control variable c and measured variable z and the associated times the current working point and the sensitivity of the therapeutic measured variable z of a person can be calculated with regard to change of the therapeutic control variable c in an evaluation unit 47.

As a measure for this sensitivity, a sensitivity F of the respective patient to the respective therapy or treatment can be determined at a working point, which in the range of the standard value $c_N$ or of the working point is equal to the relative increase dz/dc of the physiological measured variables z in the case of an increase of the respective active substance value c.

A more precise setting of the measured variable z can—if the respective dependency of the measured variable z on the control variable at the respective working point is known—be made more easily. In addition, the possibility exists to find out how strongly changes of the control variable c have an impact on the measured variable z. It is thus not only possible in the event of awareness of the dependency of control variable c on the measured variable z at a working point to quantify linear displacements of the control variable-measured variable curve, but rather also to obtain changes of its slope at the working point—and thus to make a statement on how sensitively the measured variable z will respond to slight changes of the control variable c from the working point.

In order to obtain an up-to-date control variable-measured variable curve at any time, in the event of therapy, or, for example, in the event of any taking of medicaments or treatment, the control variable c or treatment intensity, for example, the dose of a medication, is changed around a working point.

The respective value of the control variable c is assigned to the respective treatment, for example, the active substance quantity of the medication or medicament located in the medicament blister can already be stored during the production of a medicament blister (FIGS. 5, 6). Alternatively, during the administration of the medicament the respective active substance quantity can also be measured and stored (FIGS. 7, 8). The storage of the treatment intensity occurs independently of the value of the measured physiological measured variable z, for example, independently of the measured blood pressure. Thus, a point set arises in the control variable-measured variable curve, which reflects both the variation of the control variable as well as the variation of the measured variable z. From this point set depicted in FIG. 4, through a mathematical procedure, for example, fitting a straight line, the current slope of the curve at the working point, i.e., for the current dosage can be determined, which corresponds to the current sensitivity of the measured variable z to changes in the control variable at the working point.

The control variable or treatment intensity is not kept completely constant during the therapy, but rather changes with any therapy application, for example, with any taking of medication. The currently administered value in each case of the control variable is stored, even as the value of the current measured variable z. Thus, in the control variable-measured variable curve a two-dimensional point set 31 arises, which reflects both the variation of the control variable as well as the variation of the measured variable z. The measured variable z is now—as described above—still influenced by disturbance values, measurement errors and changes of the original control variable-measured variable curve 32, but in addition also by the respective value of the control variable. Assuming that disturbance values and measurement errors are distributed stochastically and the control variable-measured variable curve changes only slowly, therefore not only the mean value of the measured variable z, but rather also, for example, by fitting a straight line 33, the slope dz/dc of the curve at the working point and thus the sensitivity of the measured variable z to changes in the control variable can be determined from the existing point set. If necessary, a further approximation of a known curve 34 can also be made. The more measuring points are available, the less can the influence of the variation of the control variable be in comparison to the influence of the measurement errors and disturbance values and minimal variations of the control variable can also suffice in the case of an appropriately long observation.

As already mentioned, the control variable c of the treatment is not necessarily the dosage of a medication. The possibility also exists to use other treatment intensities of therapeutic interventions as control variables, which have a controllable or varied control variable. Accordingly, in the case of light therapy the intensity of the light can be changed, in the case of electromagnetic radiation also the intensity or the wave length, in the case of heat-/cold-therapy the temperature, in the case of all of these therapies the duration of the exposure, etc. Similar adjustable control variables can be found in the acoustics, mechanics, nutrition, etc.

Also, the measured variable z can in principle be any quantitatively measurable value, which is influenced by the therapy, therefore, for example, blood or urine, blood pressure, ECG parameters, pulse frequency, body temperature, etc.

During the therapy, pairs (c, z) regularly arise from control variable- and measured variable values. For the fitting of the control variable-measured variable curve all of these previously measured control variable-measured variable pairs can be used. In order to identify changes, it can, however, also make sense to use only the data from a predetermined time period, for example, from the last week or the last month. If it is known that certain parameters as disturbance values also influence the measured variable z—thus the blood pressure depends strongly on the time of day and is often different in the morning than in the evening—only specific value pairs can be included or excluded—depending on the value of the disturbance value. Likewise, value pairs can be excluded, which are obviously statistical outliers, because, for example, the measured variable z is significantly different in the sense of an outlier from the other previously measured variables z.

The variation of the control variable can follow a specific specification, therefore, consist of a predetermined sequence of values in terms of a deterministic signal, or also be purely accidental, therefore, have the characteristic of a noise. The invention provides that each change of the control variable c is stored and is kept available. Thus, for instance, varying treatment intensities can either be stored in the case of the production of medicaments 102 or in their administration of the medicament 102 or be determined only in the course of the treatment, in order to be able subsequently to determine the control variable-measured variable point clouds.

The current values of the control variable c are stored separately for each therapy and are available for the later processing. Thus, for instance, the exact, but process-related quantity fluctuating around a statistical average value of an active substance dripped on carrier tablets or excipients 120 in the course of the production and packaging are stored together in a storage unit or a control variable storage unit 45 of a medication dispensing device, for example, a medicament blister 101, 111.

In addition to the value of the control variable c, the time, at which the administration is carried out, therefore, for example, when a medication or medicament 102 is taken, and the time, when the measurement of the measured variable z is made, i.e. either immediately after intake, after hours, or only after days, etc., also influence the measurement result. In order to also take into account these effects, not only the value of the control variable c can be varied, but rather also the time of each individual therapy application and/or the time of the measurement of the measured variable z.

Additional significance can be conferred to the examination, while after setting a therapeutic intervention a measurement is taken not only once—at one time—, but rather over a longer period of time and repeatedly, if necessary, continuously the course of a measured variable z is observed. If the measurement series is carried out with each application, a statement on the influence of the control variable c on the measured variable z can be determined from the comparison of the signal paths after the individual interventions.

Furthermore, it can be determined by using a cross-correlation analysis, whether time constants of the influence of the measured variable z are dependent on the value of the control variable or in general a possibly given time lag between the application of the control variable c and the observable changes in the measured variable z are taken into account.

Generally, in the course of the evaluation a model for the relationship of the control- and the measured variable c; z can be formulated in terms of a transmission system and the structural parameters of this model can be estimated in terms of a system analysis by means of mathematical methods.

In FIG. 5 a method according to an embodiment of the invention is depicted in detail, which is used to create a number of medicaments 102, which are provided with a predetermined active substance. The goal of the method is to keep available the respective active substance quantity contained in the medicament 102 in the form of an active substance value c simultaneously with the production of the medicament 102. In particular, the active substance value c should be kept available for retrieval in a control variable storage unit 45.

At the beginning of the process the average target active substance quantity of the medicament 102 in the form of a standard value $c_N$ is prescribed by a doctor or set at a standard value. In addition, a maximum deviation $\Delta c$ from this standard value $c_N$ is predetermined. The active substance value c is thus within an interval $c_N \pm \Delta c$. The active substance value c can thereby either be selected or the loading of the medicament 102 with the predetermined active substance is undertaken with a certain error tolerance, so that the medicaments 102 ultimately created contain an active substance quantity, which corresponds to an active substance value within the interval $c_N \pm \Delta c$.

If the active substance value c is predetermined, the active substance c can be assigned to the respective medicament and be stored in the previously mentioned storage 105.

If the created active substance value c is subject to a certain variation in that the production of the respective medicament 102 cannot be carried out exactly, the quantity of the active substances located in the medicament 102 is measured in a subsequent step and the measurement result is assigned as active substance value c to the respective medicament 102. After the creation of the medicament 102 both the medicament 102 as well as the active substance value of the medicament 102 are kept available.

Depending on the respective medicament or dependent on the respective active substance or active ingredient the maximum deviation $\Delta c$ from the standard value $c_N$ is between 10% and 20%. In particular, the deviation from the standard value is greater than 5% or greater than 10%.

Schematic representations of the procedure for the production of medicaments according to two preferred embodiments of the invention as well as two devices 130, 140 for the creation of medicaments 102 are depicted in FIGS. 5 and 6. An active substance fluid 121 containing a medicament active substance, for example, an emulsion, solution or suspension, in the present case an active substance solution, is available in a storage container. Both devices 130, 140 depicted in FIGS. 5 and 6 have in each case a supply unit 131, 141, with which the excipients 120 in the form of powder tablets are made available. The container filled with the active substance fluid 121 has an outlet at its lower end, which opens into a portioning unit 132, 142. The portioning unit 132, 142 provides droplets 122 of the active substance fluid 121 and lets these drip onto the excipient 120 supplied by the supply unit 131, 141.

Furthermore, the device has a control unit 133, 143, which controls the portioning unit 132, 142 and sets the quantity of the active substance to be dispensed by the portioning unit 132, 142. The control unit 133 receives on its part the active substance quantity to be set in each case for the medicament, wherein a standard value of $c_N$ and an interval $\Delta c$ around this standard value $c_N$ are given.

If the portioning unit 132 for producing the medicament 102, depicted in FIG. 5, operates with sufficient precision, a separate active substance value c in the form of a random value can be predetermined for the creation of medicaments 102 with a certain variance $\Delta c$ of the individual active substance values c for each individual medicament 102. This random value is located constantly within the interval $c_N \pm \Delta c$. The distribution of the individual random values follows a specific distribution. In the present embodiment a uniform distribution within the predetermined interval $c_N \pm \Delta c$ is selected as the distribution for the random values.

If, therefore, the portioning unit 132 supplies medicament 102 with a sufficiently precisely determinable active substance quantity of active substance fluid, the respective active substance value c contained in the medicament 102 can be assigned directly to the respective medicament 102 and can be kept available together with an identification number for this medicament 102. In this case, the control unit 133 is designed to control the size of the quantity of the active substance fluid 121 dispensed from the portioning unit 132. The control unit 133 determines the respective active substance quantity contained in the medicament 102 within an interval $c_N \pm \Delta c$ around the standard value $c_N$, for example, as a random value.

With a less precise control unit 143 or portioning unit 142, a statistical distribution of the active substance quantities applied to the individual excipients 120 can already be attained by the production-related tolerances. Such an embodiment of the invention is depicted in FIG. 6. This embodiment also has a supply unit 141 for excipients 120, a container for the active substance fluid 121, a control unit 143, a portioning unit 142. In addition, however, this device 140 has a unit 144 for determining the size of the droplets 122 applied by the portioning unit 142 on the excipient 120. In order to determine the respective active substance quantity assigned to the medicament 102 in the form of an active substance value c, the control signal of the control unit 143 impressed on the portioning unit 132, 142, contrary to the embodiment depicted in FIG. 5, is not consulted, here the impressed signal would be distorted especially by the production-related tolerances. Rather the size of the droplet 122 of the active substance fluid 121 dispensed by the portioning unit 142 is measured separately and directly. The thus determined measured value for the size of the droplet 122 dripped on to the excipient 120 is kept available and stored as active substance value c for the respective medicament 102.

After production of the medicament there are now basically two possibilities for dispensing and administering the medicament 102 created to a patient: According to a first embodiment of the invention the individual medicaments are dispensed immediately after their production directly to the patient. The patient receives the medicaments created, wherein the respective active substance value c assigned to the medicament 102 is transmitted directly to a control variable storage unit 45 depicted in FIG. 3, which is assigned to the respective patient. In this way, for example, a variety of medicaments 102 can be rapidly and cost-effectively created in hospitals or in studies performed, without a complicated packaging process being required.

Alternatively, a medicament blister 101 depicted in FIG. 7 can be created, in which the medicament 102 thus created can be inserted. The individual medicaments 102 are immediately inserted after their creation in each case into individual pockets 103 of the medicament blister 101. The active substance value c assigned to the respective medicament 102 as well as a key $k_1, \ldots, k_n$ characterizing the respectively predetermined pocket 103 of the medicament blister 101 is transmitted to a storage 105 and stored in the latter. In the embodiment of the invention depicted in FIG. 5 the storage 105 is located together with a controller 104 on a microchip, which is arranged directly on the medicament blister 101. The microchip also has RFID functionality and allows the controller 104 to communicate with external data communications units and in particular permits the data transfer of active substance values c to the control variable storage unit 45. For each medicament 102 in each case a key $k_1, \ldots, k_n$ characterizing the respective pocket 103, as well as the respective active substance quantity of the medicament 102 located in the respective pocket is stored as digital active substance value c. The controller 104 keeps available the respective active substance quantity as well as the key $k_1, \ldots, k_n$ assigned in each case for joint retrieval.

After inserting the medicament 102 into the pockets 103 of the medicament blister 101 or container the pockets 103 are closed. The pockets 103 are only opened by the patient 44 immediately for taking the respective medicament 102. The controller 104 detects the opening of the respective pocket 103 and keeps the key $k_1, \ldots, k_n$ characterizing in each case the last opened pocket 103 available together with the active substance value c of the medicament located in this pocket 103. It is thus possible to retrieve from the respective medicament blister 101 or from the controller 104 located in it, how high the active substance value c of the medicament 102 located in the last opened pocket 103 is or was. A variety of different methods are available from the prior art for determining when or whether a pocket 103 has been opened. In particular, it is possible to install conducting paths in the area of the foil closing the pockets 103, which are interrupted during the opening of the pockets 103. In this way, the controller 104 can determine that the respective pocket 103 is opened and makes available the active substance value c assigned to the respective pocket 103 upon request.

In determining the dose-response curve it is advantageous that the respective active substance value c of the last opened pocket 103 is transmitted to the control variable storage unit 45, wherein the respective active substance value c together with the respective dispensing time, that is, the time, at which the patient has opened the pocket 103, is stored. In addition, a personal identification number of the respective patient 44 is added to the thus stored data set.

According to a further alternative embodiment of the invention, which otherwise corresponds to the embodiment depicted in FIG. 7, it can also be provided not to store the individual active substance values in a storage located on the medicament blister 111, but rather to keep them available on a storage located on a—not depicted—central server. Such an embodiment of the invention is depicted in detail in FIG. 8. On the other hand, the individual medicaments are located in a predetermined pocket 103 of a medicament blister or medicament blister 111. The medicament blister 111 has a controller 114, on which a predetermined identification $m_1, \ldots, m_n$ characterizing the medicament blister 111 is stored. Moreover, as also in the previous embodiment of the invention, each individual pocket 103 of the medicament blister 111 in each case is assigned a characterizing key $k_1, \ldots, k_n$. In the creation of a medicament 102 in each case a data set is created, which has the active substance quantity c assigned to the medicament 102, the identification assigned to the medicament blister 111, as well as a key $k_1, \ldots, k_n$ characterizing the respective pocket 103 of the medicament blister 111. These data sets are transmitted jointly to the central server, which keeps available the respective active substance value c of the medicament 102 located in the pocket 103 during transmission of the identification $m_1, \ldots, m_n$ characterizing the medicament blister 111 as well as of the key $k_1, \ldots, k_n$ characterizing the respective pocket 103. As also in the preceding example, the pockets 103 of the medicament blister 111 containing the medicament 102 are closed after the insertion of the medicament 102 and opened only immediately before taking the medicament 102 by the patient 44. The respective key $k_1, \ldots, k_n$ of the last opened pocket 103 is transmitted together with the identification $m_1, \ldots, m_n$ of the respective medicament blister 111 to the central server and the central server transmits the active substance quantity c stored on it and assigned to the key $k_1, \ldots, k_n$ as well as the identification $m_1, \ldots, m_n$ back to the patient 44. Finally, the respective active substance value c is transmitted to the control variable storage unit 45, wherein the respective active substance value c together with the respective dispensing time is stored in a storage of the control variable storage unit 45 assigned to the patient 44.

The invention claimed is:

1. A method for producing a number of medicaments with a predetermined active substance and for a simultaneous supply of an active substance value indicating an active substance quantity contained in a medicament, which comprises the steps of:
   predetermining a standard value cN and a maximum deviation Δc from the standard value for the active substance quantity to be determined in each case of the medicament, wherein the active substance value being selected or predetermined within an interval cN++/−Δc; and
   creating the medicament by adding the active substance quantity of the active substance, the active substance quantity corresponds to the active substance value, and that a created active substance value is assigned to the medicament and the created active substance value is kept available together with the medicament, the creating step further comprises:
   making available a number of excipients; and
   adding a predetermined quantity of the active substance into an excipient and the active substance being received by an excipient substance of the excipient.

2. The method according to claim 1, which further comprises predefining active substance values of the medicaments as following a predetermined distribution, namely uniformly distributed or discretely distributed, random values within the interval cN++/−Δc.

3. The method according to claim 1, wherein the maximum deviation from the standard value is greater than 5% of the standard value.

4. The method according to claim 1, which further comprises:
   making available an active substance fluid containing the active substance;
   dripping the predetermined quantity of the active substance fluid onto the excipient and is received by the excipient substance of the excipient, wherein during a fall of a respective droplet of the active substance fluid in a direction of the excipient a volume of the respective droplet is determined, and that for the medicament a respective size of the respective droplet is assigned as the active substance value to the medicament created and the medicament is kept available together with the active substance value associated with it.

5. The method according to claim 1, which further comprises:
   assigning the medicaments created for a patient and dispensed to the patient; and
   storing a respective active substance value together with a respective dispensing time in a documentation memory assigned to the patient.

6. The method according to claim 1, which further comprises:
   inserting the medicament created into a predetermined pocket of a medicament blister; and
   transmitting together the active substance value assigned to the medicament as well as a key characterizing the predetermined pocket of the medicament blister to a memory disposed on a controller disposed on the medicament blister, and that the key characterizing the predetermined pocket as well as the active substance quantity of the medicament located in the predetermined pocket are kept available for retrieval from the controller.

7. The method according to claim 6, which further comprises:
   closing pockets of the medicament blister containing the medicament after insertion of the medicament; and
   opening one of the pockets by a patient before taking the medicament, that the opening of the pocket is detected by the controller disposed on the medicament blister, that the respective active substance value of the medicament disposed in a last opened pocket is kept available separately and/or additionally, by the controller, and that, if necessary, the respective active substance value is transmitted to a documentation server, wherein the respective active substance value is stored together with a respective dispensing time in a documentation memory of the documentation server assigned to the patient.

8. The method according to claim 1, which further comprises:
   inserting the medicament created into a predetermined pocket of a medicament blister having a controller storing a predetermined identification characterizing the medicament blister; and
   transmitting the active substance quantity associated with the medicament, the predetermined identification associated with the medicament blister, and a key characterizing the predetermined pocket of the medicament blister jointly to a server, and the active substance value of the medicament disposed in the predetermined pocket during transmission of the predetermined identification characterizing the medicament blister as well as of the key characterizing the predetermined pocket are kept available for retrieval from the server.

9. The method according to claim 8, which further comprises:

closing pockets of the medicament blister containing the medicament after insertion of the medicament, and before taking the medicament a respective pocket is opened by a patient, that each opened pocket is detected by the controller located on the medicament blister, that the key of a last opened pocket together with the predetermined identification of the medicament blister is transmitted to the server and the server determines and keeps available the active substance quantity stored on it and associated with the key as well as the predetermined identification, and that, if necessary, the active substance value is transmitted to a control variable memory unit, wherein the active substance value together with a respective dispensing time are stored in a memory of the control variable storage unit assigned to the respective patient.

10. The method according to claim 1, wherein the maximum deviation from the standard value is greater than 10% of the standard value.

11. The method according to claim 4, which further comprises:

providing the active substance fluid as a solution, an emulsion or a suspension; and providing the excipients as powder tablets.

* * * * *